United States Patent
Wang et al.

(10) Patent No.: US 7,294,252 B2
(45) Date of Patent: Nov. 13, 2007

(54) NOX SENSOR AND METHODS OF USING THE SAME

(75) Inventors: Da Yu Wang, Troy, MI (US); Walter T. Symons, Grand Blanc, MI (US); Robert Jerome Farhat, Grosse Point Park, MI (US); Sheng Yao, Macomb, MI (US); Joachim Kupe, Davisburg, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 11/538,252

(22) Filed: Oct. 3, 2006

(65) Prior Publication Data

US 2007/0080075 A1  Apr. 12, 2007

Related U.S. Application Data

(60) Provisional application No. 60/725,055, filed on Oct. 7, 2005.

(51) Int. Cl.
*G01N 27/407* (2006.01)
(52) U.S. Cl. ............... 205/781; 205/785; 204/424; 73/23.31
(58) Field of Classification Search .............. 205/781, 205/785; 204/424, 426; 73/23.31
See application file for complete search history.

(56) References Cited

U.S. PATENT DOCUMENTS

| | | | | |
|---|---|---|---|---|
| 4,927,517 A | * | 5/1990 | Mizutani et al. | 204/406 |
| 5,705,129 A | * | 1/1998 | Takahashi et al. | 422/90 |
| 5,948,964 A | * | 9/1999 | Kato | 73/23.31 |
| 6,277,267 B1 | * | 8/2001 | Geloven et al. | 205/781 |
| 6,287,439 B1 | * | 9/2001 | Kato et al. | 204/425 |
| 6,413,397 B2 | * | 7/2002 | Hasei et al. | 204/424 |
| 7,074,319 B2 | | 7/2006 | Wang et al. | |
| 2003/0062264 A1 | | 4/2003 | Kitanoya et al. | |

FOREIGN PATENT DOCUMENTS

GB  2347219 A  8/2000

* cited by examiner

*Primary Examiner*—Kaj K. Olsen
(74) *Attorney, Agent, or Firm*—Paul L. Marshall (57) ABSTRACT

Disclosed herein are NOx sensors and methods of using the same. In one embodiment, a method for sensing NOx comprises: contacting a first NOx electrode with the gas, contacting a second NOx electrode with the gas, determining a $NO_2$ emf between the first NOX electrode and a first reference electrode, determining a NOx emf between the second NOx electrode and a second reference electrode, and determining a $NO_2$ concentration and a NO concentration using the $NO_2$ emf and the NOx emf. The first electrode can be at a first temperature of greater than or equal to about 700° C., and the second electrode can be at a second temperature of about 500° C. to about 650° C.

11 Claims, 7 Drawing Sheets

FIG. 7

NOX SENSOR AND METHODS OF USING THE SAME

CROSS REFERENCE TO RELATED APPLICATIONS

This application claims priority to U.S. Provisional Application No. 60/725,055, filed Oct. 7, 2005, and incorporated herein by reference in its entirety.

BACKGROUND

Exhaust gas generated by combustion of fossil fuels in furnaces, ovens, and engines contain, for example, nitrogen oxides (NOx), unburned hydrocarbons (HC), and carbon monoxide (CO), which are undesirable pollutants. Vehicles, e.g., diesel vehicles, utilize various pollution-control after treatment devices (such as a NOx absorber(s) and/or Selective Catalytic Reduction (SCR) catalyst(s)), to reduce NOx. For diesel vehicles using SCR catalysts, NOx reduction can be accomplished by using ammonia gas ($NH_3$). In order for SCR catalyst to work efficiently and to avoid pollution breakthrough, an effective feedback control loop is needed. To develop such technology, the control system needs reliable commercial NOx sensors.

Some NOx sensor designs use an impedance oxide method to measure the partial pressure of NOx. In this design, NOx gases interact with semiconducting oxides, thereby causing an electrical impedance change in the oxides. These sensors cannot effectively maintain calibration. Further, these sensors experience selectivity problems wherein other gasses; for example, CO, hydrogen ($H_2$), HC, $NH_3$, $CO_2$, and water ($H_2O$), will interfere with NOx sensing.

Therefore a cost effective sensor that can reliably measure NOx under exhaust gas conditions would benefit the control system.

SUMMARY

Disclosed herein are NOx sensors and methods of using the same. In one embodiment, a method for sensing NOx comprises: contacting a first NOx electrode with the gas, contacting a second NOx electrode with the gas, determining a $NO_2$ electromotive force (emf) between the first NOX electrode and a first reference electrode, determining a NOx emf between the second NOx electrode and a second reference electrode, and determining a $NO_2$ concentration and a NO concentration using the $NO_2$ emf and the NOx emf. The first electrode can be at a first temperature of greater than or equal to about 700° C., and the second electrode can be at a second temperature of about 500° C. to about 650° C.

In another embodiment, a method for sensing NOx comprises: contacting a first NOx electrode with the gas, contacting a second NOx electrode with the gas, determining a $NO_2$ electromotive force (emf) between the first NOX electrode and a reference electrode, determining a NOx emf between the second NOx electrode and the reference electrode, and determining a $NO_2$ concentration and a NO concentration using the $NO_2$ emf and the NOx emf. The first electrode can be at a first temperature of greater than or equal to about 700° C., and the second electrode can be at a second temperature of about 500° C. to about 650° C.

In one embodiment, a NOx sensor element comprises: a first NOx electrode, a second NOx electrode, a first reference electrode, a second reference electrode, and an electrolyte. The electrolyte is disposed between the first NOx electrode and the first reference electrode. The first NOx electrode is capable of operating at a first temperature of greater than or equal to about 700° C., while the second NOx electrode is capable of operating a second temperature of about 500° C. to about 650° C. During use, a first NOx emf can be established between the first NOx electrode and the first reference electrode, and a second NOx emf can be established between the second NOx electrode and the second reference electrode.

In one embodiment, a NOx sensor comprises: a NOx sensing element, a housing, wherein the NOx sensor element is disposed in the housing, and a catalyst located upstream of the sensor element. The housing has an inlet for receiving a gas such that the gas can contact the sensor element. During use of the sensor, a gas contacts the catalyst prior to contacting the sensor element, and hydrocarbons, carbon monoxide, ammonia, and/or hydrogen in the gas are converted to nitrogen, carbon dioxide, and/or water.

The above described and other features are exemplified by the following figures and detailed description.

DRAWINGS

Referring now to the figures, which are exemplary embodiments, and wherein like elements are numbered alike.

DETAILED DESCRIPTION

Figure 1:
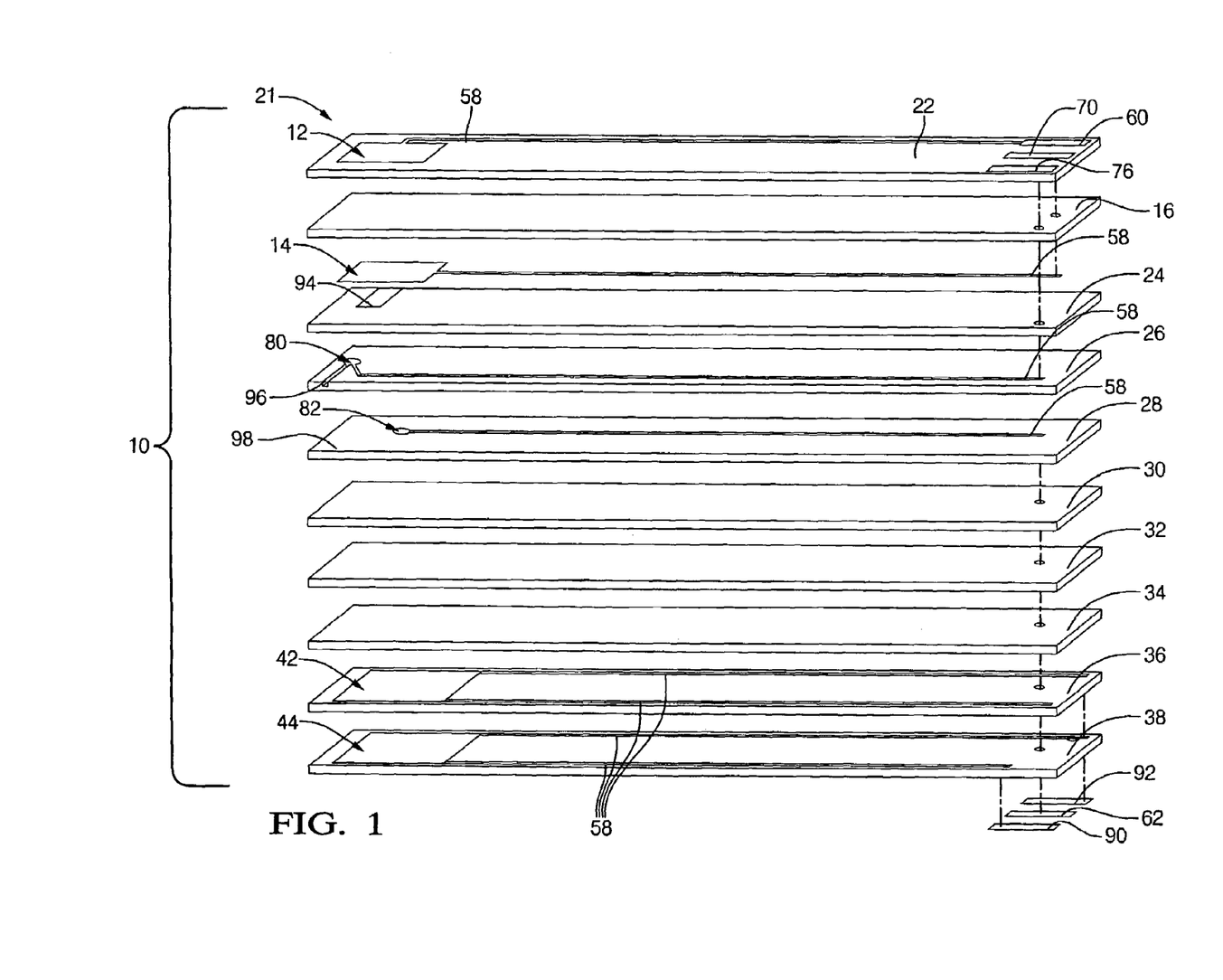
FIG. 1 is an exploded view of an exemplary planar sensor element.
Figure 2:
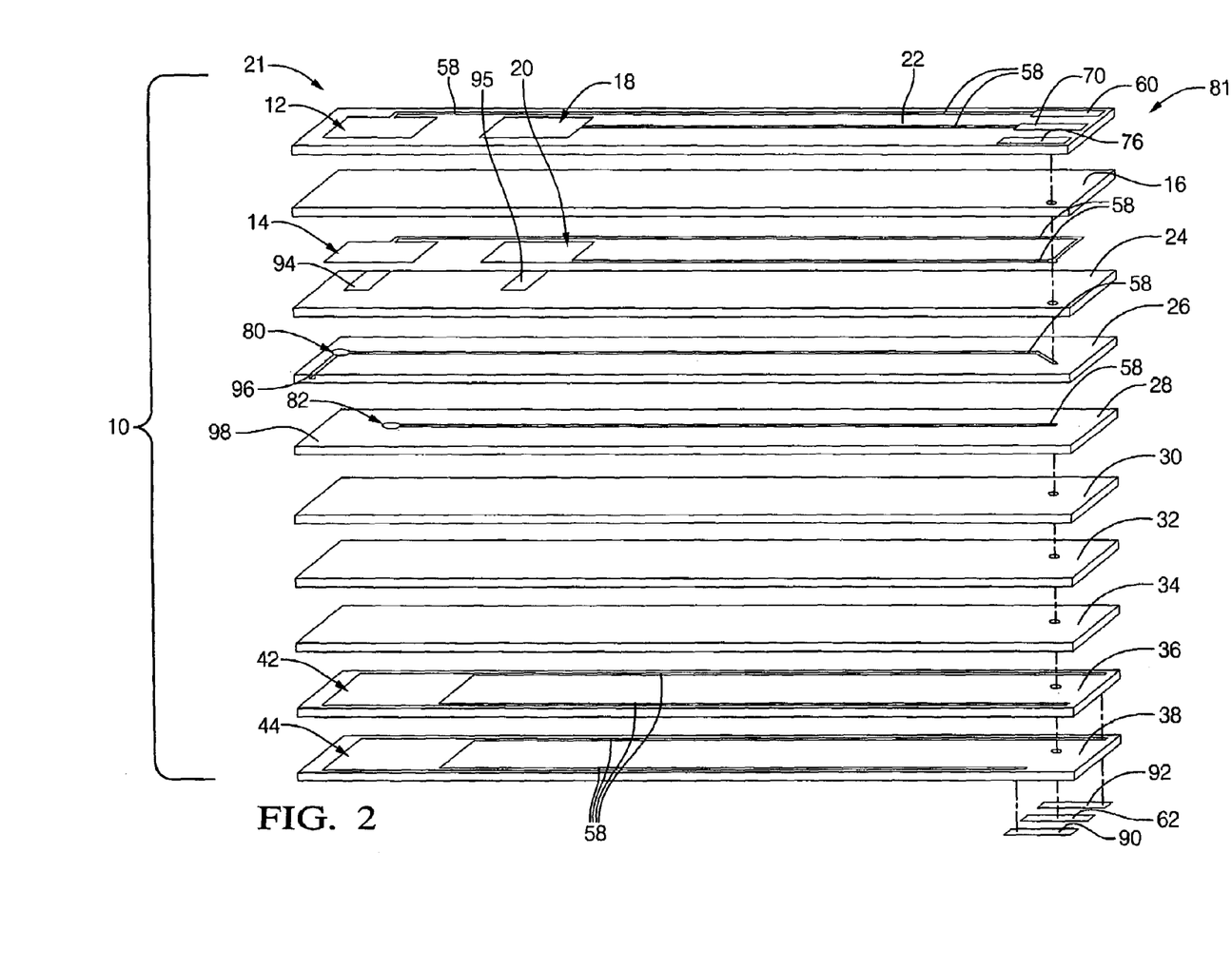
FIG. 2 is an exploded view of an exemplary planar sensor element.

Referring to FIGS. 1 and 2, exemplary sensing elements 10,100 comprise a NOx sensing cell (12/16/14) comprising a first sensing electrode 12, a first reference electrode 14 and an electrolyte layer 16, and optionally (as shown in FIG. 2) a second NOx sensing cell (18/16/20) comprising a second sensing electrode 18, a second reference electrode 20 and the electrolyte layer 16. The NOx sensing cells 12/16/14, 18/16/20 are disposed at a sensing end 21 of the sensing element 10. The sensing element 10 comprises insulating layers 22, 24, 28, 34, 36, 38, and active layers, which include the electrolyte layer 16 and layers 26, 30, and 32. The active layers can conduct oxygen ions, where the insulating layers can insulate sensor components from electrical and ionic conduction. In an exemplary embodiment, the electrolyte layer 16 is disposed between insulating layers 22 and 24, active layer 26 is disposed between insulating layers 24 and 28, and active layers 30 and 32 are disposed between insulating layers 28 and 34.

The sensing elements 10,100 can further comprise a temperature sensor (not shown), an air-fuel sensing cell comprising the active layer 26 along with an electrode 80 and an electrode 82 (80/26/82), a heater 44 disposed between the insulating layers 36 and 38, and an electromagnetic shield 42 (also known as a ground plane layer) disposed between the insulating layers 34 and 36. A first inlet 94 is defined by a first surface of the insulating layer 24 and by a surface of the electrolyte 16, proximate the first reference electrode 14. A second inlet 95 is defined by a first surface of the insulating layer 24 and by a surface of the electrolyte 16, proximate the second reference electrode 20. A third inlet 96 is defined by a first surface of the active layer 26 and a second surface of the insulating layer 24, proximate the electrode 80. An fourth inlet 98 is defined by a first surface of the active layer 26 and a second surface of the insulating layer 24, proximate the electrode 80. In addition, the sensing elements 10,100 comprise electrical leads (58), contact pads (60, 64, 70, 76, 90, 92), additional ground plane layer(s) (not shown), and the like.

The first and second sensing electrodes 12, 18 are disposed in physical and ionic communication with electrolyte 16 and can be disposed in fluid communication with a sample gas (e.g., a gas being monitored or tested for its NOx concentration). The electrode materials have NOx sensing capability (e.g., catalyzing NOx gas to produce an electromotive force (emf)), electrical conducting capability (conducting electrical current produced by the emf), and gas diffusion capability (providing sufficient open porosity so that gas can diffuse throughout the electrode and to the interface region of the electrodes 12, 18 and electrolyte 16). The electrodes 12, 16 can comprise material(s) with the above properties at the selected operating temperatures. These materials include $YbCrO_3$, $LaCrO_3$, $ErCrO_3$, $EuCrO_3$, $SmCrO_3$, $HoCrO_3$, $GdCrO_3$, $NdCrO_3$, $TbCrO_3$, $ZnFe_2O_4$, $MgFe_2O_4$, and $ZnCr_2O_4$.

The electrodes can be formed to operate at desirable temperatures, depending upon the gas to be sensed. For example, the sensing electrode can operate at a temperature of about 200° C. to about 400° C. In other embodiments, the sensing electrode(s) can operate at a temperature of about 500° C. to about 650° C., a temperature of about 650° C. to about 700° C., or a temperature of greater than or equal to about 700° C. The operating temperature of the electrodes can be tailored with the use of dopant(s). These dopants can include: Ba (barium), Ti (titanium), Ta (tantalum), K (potassium), Ca (calcium), Sr (strontium), V (vanadium), Ag (silver), Cd (cadmium), Pb (lead), W (tungsten), Sn (tin), Sm (samarium), Eu (europium), Er (Erbium), Mn (manganese), Ni (nickel), Zn (zinc), Na (sodium), Zr (zirconium), Nb (niobium), Co (cobalt), Mg (magnesium), Rh (rhodium), Nd (neodymium), Gd (gadolinium), and Ho (holmium), as well as combinations comprising at least one of the foregoing dopants.

For example, the NOx electrode can comprise $ZnFe_2O_4$ for operating at sensing temperatures of about 675° C. to about 725° C. (e.g., about 700° C.), $MgFe_2O_4$ for operating at sensing temperatures of about 650° C. to about 700° C. (e.g., about 675° C.), $LaCrO_3$, $ErCrO_3$, $EuCrO_3$, and/or $SmCrO_3$ for operating at sensing temperatures of about 500° C. to about 650° C. (e.g., about 600° C.), and $HoCrO_3$, $GdCrO_3$, and/or $NdCrO_3$ for operating at sensing temperatures of about 500° C. to about 550° C. (e.g., about 525° C.). In another embodiment, the NOx electrode can comprise $LaCrO_3$ doped with an element such as: Ba (for operating at sensing temperatures of about 675° C. to about 725° C., e.g., about 700° C.), Ti (for operating at sensing temperatures of about 650° C. to about 700° C., e.g., about 675° C.), and Ta (for operating at sensing temperatures of about 625° C. to about 675° C., e.g., about 650° C.), K, Ca Sr, V, Ag, Cd, Pb (for operating at sensing temperatures of about 600° C. to about 650° C., e.g., about 625° C.), W, Sn, Sm, Eu, Er (for operating at sensing temperatures of about 575° C. to about 625° C., e.g., about 600° C.), Mn, Ni, Zn (for operating at sensing temperatures of about 550° C. to about 600° C., e.g., about 575° C.), Na, Zr, Nb, Co (for operating at sensing temperatures of about 525° C. to about 675° C., e.g., about 550° C.), Mg, Rh Nd, Gd, Ho (for operating at sensing temperatures of about 500° C. to about 550° C., e.g., about 525° C.). The dopant level can be less than or equal to about 20 at %, e.g., about 5 atomic percent (at %) to about 15 at %.

In addition to the temperature, the contact resistance of the electrodes in contact with the electrolyte can be adjusted/controlled, e.g., so that the contact resistance is at least within the same order of magnitude of the electrolyte itself to enable the sensing emf to be measured mostly by external measurement devices (such as voltmeters) without much internal drop of emf voltage at the contact area. For example, in the compound of $TbCrO_3$, the contact resistance will be within the order magnitude of 100 ohm, if doped with (Mg, Ca, Sr, V, Ta, W, Nd, and/or Ni), within the order magnitude of 1,000 ohm if doped with (Co, Rh, Gd, Sn, and/or Pb), less than or equal to about 10,000 ohm if doped with (Na, Ba, La, Ti, Zr, Ag, Cd, Sm, Eu, Th, Ho, and/or Yb), and within the order of magnitude of 100,000 ohm if doped with (K, Nb, Mn, Zn, and/or Er). Doping levels can be the same as described above. Depending on the applications, different compounds can be used. For example, $Tb_4O_7$, $Cr_2O_3$, and MgO powder was mixed mechanically (with proportion weight for the formula of $ThCr_{0.8}Mg_{0.2}O_3$).

The reference electrodes 14, 20 are disposed in physical contact and in ionic communication with the electrolyte 16, and can be disposed in fluid communication with the sample gas or reference gas; preferably with the sample gas. The reference electrodes materials have oxygen catalyzing capability (e.g., catalyzing equilibrium $O_2$ gas to produce an emf), electrical conducting capability (conducting electrical current produced by the emf), and/or gas diffusion capability (providing sufficient open porosity so that gas can diffuse throughout the electrode and to the interface region of the reference electrode 14 or 20 and electrolyte 22). Possible electrode materials include platinum (Pt), palladium (Pd), osmium (Os), rhodium (Rh), iridium (Ir), gold (Au), ruthenium (Ru), and the like, as well as mixtures comprising at least one of the foregoing materials. The electrode can include metal oxides such as zirconia and alumina that can increase the electrode porosity and increase the contact area between the electrode and the electrolyte.

The electrolyte layer 16 has oxygen ion conducting and fluid separation (limiting fluid communication of the sample gases on each side of the electrolyte layer 16) capabilities. The electrolyte layer 16 can be any size capable of providing sufficient ionic communication for the NOx sensing cell (12/16/20) or cells (12/16/20 and 18/16/20). The electrolyte layer 16 can be the entire length and width of the sensing element 10 or portions thereof. Possible electrolyte layer materials include zirconium oxide (zirconia), cerium oxide (ceria), calcium oxide, yttrium oxide (yttria), lanthanum oxide, magnesium oxide, alumina oxide, indium oxide and the like, as well as combinations comprising at least one of the foregoing electrolyte materials, such as yttria doped zirconia, $LaGaO_3$, $SrCeO_3$, $BaCeO_3$, and $CaZrO_3$.

The air-fuel sensing cell (80/26/82) can detect the air to fuel ratio of the sample gas. When a constant potential is applied to electrodes 80 and 82, the current through the air-fuel sensing cell 80/26/82 is limited by the oxygen available in the inlets 96, 98 and at the electrodes 80, 82. Therefore, by measuring the potential at the air-fuel sensing cell 80/26/82, the processor can determine the air-to-fuel ratio of the gas. This same cell can also be used for sensing the temperature of the gas. In this mode an AC signal will be applied to the electrode 80 and 82, and the impedance of the electrolyte 26 between the two electrodes 80 and 82 is used for temperature determination.

The heater 44 can be employed to maintain the sensing element 10 at a selected operating temperature. The heater 44 can be positioned as part of the monolithic design of the sensing element 10, for example between insulating layer 36 and insulating layer 38, in thermal communication with the air-fuel sensing cell 80/26/82 and the sensing cells 12/16/14, 18/16/20. In other embodiments, the heater could be in thermal communication with the cells without necessarily being part of a monolithic laminate structure with them, e.g., simply by being in close physical proximity to a cell. More specifically, the heater can be capable of maintaining the sensing end 21 of the sensing element 10 at a sufficient temperature to facilitate the various electrochemical reactions therein. The heater can be a resistance heater and can comprise a line pattern (connected parallel lines, serpentine, and/or the like). The heater can comprise, for example, platinum, aluminum, palladium, and the like, as well as combinations comprising at least one of the foregoing, oxides comprising at least one of the foregoing metals. Contact pads, for example, the fourth contact pad 66 and the fifth contact pad 68, can transfer current to the heater from an external power source.

The temperature sensor (not shown) comprises any temperature sensor capable of monitoring the temperature of the sensing end 21 of the sensing elements 10,100, such as, for example, an impedance-measuring device or a metal-like resistance-measuring device. The metal-like resistance temperature sensor can comprise, for example, a line pattern (connected parallel lines, serpentine, and/or the like). Some possible materials include, but are not limited to, electrically conductive materials such as metals including platinum (Pt), copper (Cu), silver (Ag), palladium (Pd), gold (Au), tungsten (W), as well as combinations comprising at least one of the foregoing.

Disposed between the insulating layers 34 and 36 can be an electromagnetic shield 42. The electromagnetic shield 42 isolates electrical influences by dispersing electrical interferences and creating a barrier between a high power source (such as the heater) and a low power source (such as the temperature sensor and the gas sensing cell). The shield can comprise, for example, a line pattern (connected parallel lines, serpentine, cross hatch pattern, and/or the like). Some possible materials for the shield can include those materials discussed above in relation to for the heater.

At the sensing end 21 of the sensing elements 10,100, the electrical leads 58, are disposed in physical contact and in electrical communication with electrodes 12, 14, 18, 20, 80, 82. Further, electrical leads 58 are disposed in electrical communication with the heater 44 and the electromagnetic shield 42. Each electrical lead extends from a contact pad or via toward the sensing end 21. Electrical leads not disposed on a top surface or a bottom surface of the sensing element 10,100 are in electrical communication with the contact pads through vias formed in the layers. Two sets of three contact pads are disposed at the terminal end 81 of the sensing element 10: the first, second, and third contact pads 60, 70, 76 are disposed on the upper surface of the sensing element 10, and the fourth, fifth and sixth contact pads 62, 90, 92 are disposed on the lower surface of the sensing element 10. The first, second, third, and fourth contact pads 60, 62 70, 76 are in electrical communication with a processor (not shown), and the fifth and sixth contact pads are in electrical communication with an external power source (not shown).

The insulating layers 22, 24, 28, 34, 36, 38 can comprise a dielectric material such as alumina (i.e., aluminum oxide ($Al_2O_3$)), and the like. Each of the insulating layers can comprise a sufficient thickness to attain the desired insulating and/or structural properties. For example, each insulating layer can have a thickness of up to about 200 micrometers or so, depending upon the number of layers employed, or, more specifically, a thickness of about 50 micrometers to about 200 micrometers. Further, the sensor element 10 can comprise additional insulating layers to isolate electrical devices, segregate gases, and/or to provide additional structural support.

The active layers 26, 30, and 32 can comprise material that, while under the operating conditions of sensing element 10, is capable of permitting the electrochemical transfer of oxygen ions. These include the same or similar materials to those described as comprising electrolyte layer 16. Each of the active layers can comprise a thickness of up to about 200 micrometers or so, depending upon the number of layers employed, or, more specifically, a thickness of about 50 micrometers to about 200 micrometers.

Figure 3:
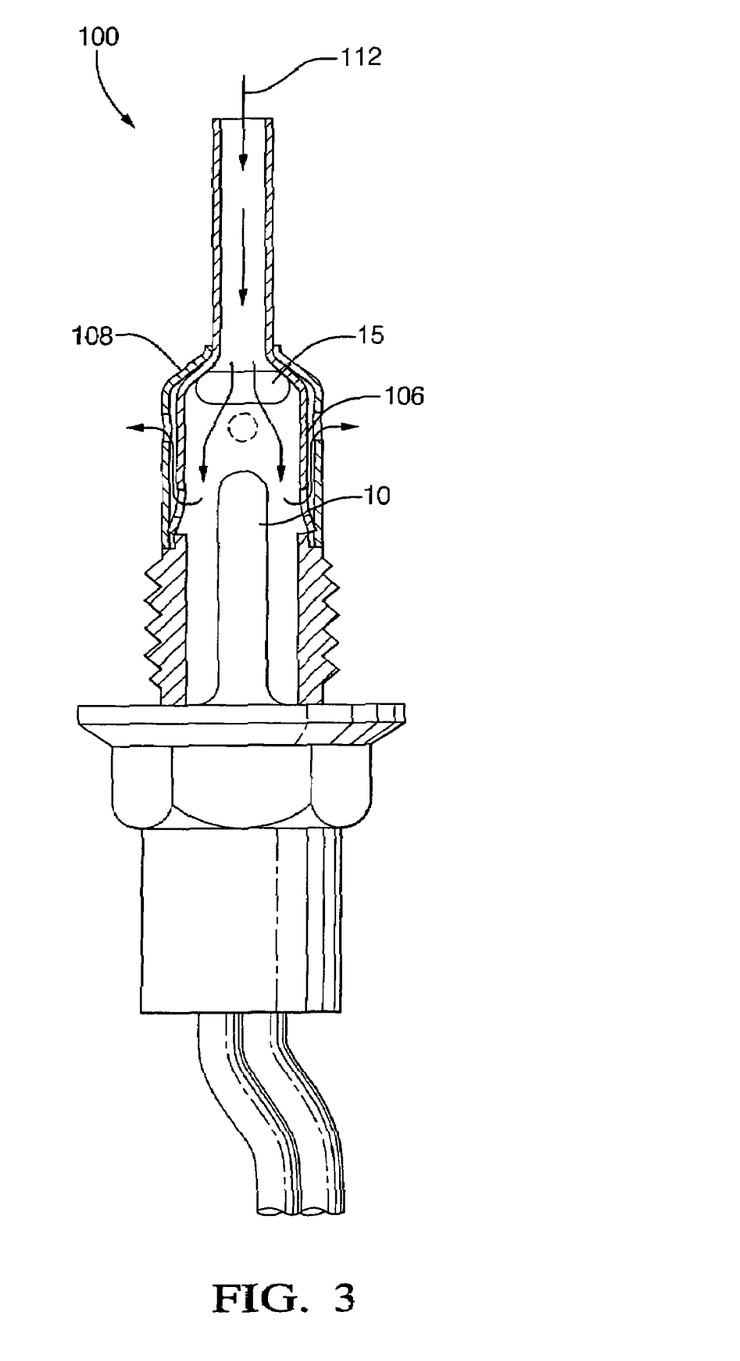
FIG. 3 is a cross-sectional view of an exemplary embodiment of a planar sensor element and casing.
Figure 4:
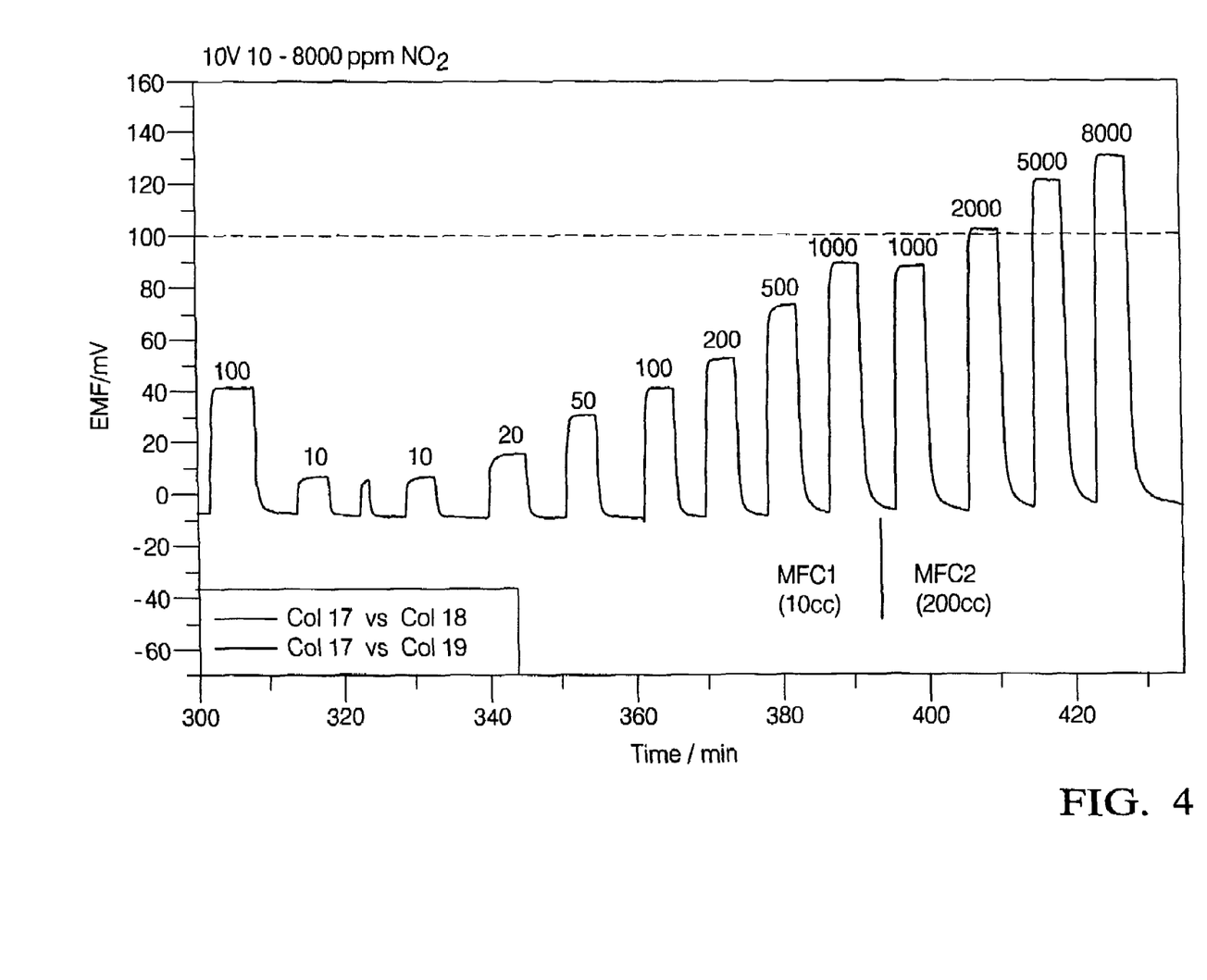
FIG. 4 is a graphical representation of sensor performance determined in 15 vol. % oxygen, balance nitrogen, with a water content of 1 vol % of the gas mixture, wherein 10 ppm to 8,000 ppm of $NO_2$ was introduced to the gas for the test.

Referring to FIG. 3, for placement in a gas stream, sensing element 10 can be disposed within a protective casing 120. The protective casing 120 can comprise an outer shield 108 having a plurality of outer shield holes 116. An inner shield 106 has a plurality of passages 114, which allows fluid to enter a space between the inner shield 106 and the outer shield 108. Outer shield holes 116 allow fluid in the space between inner shield 106 and outer shield 108 to exit the casing 120. An optional sampling tube having an inlet 112 extends from the outer shield 108. The sampling tube opens into a catalyst surrounding sensing element 10,100. Arrows are shown to illustrate the general fluid flow direction within the protective casing.

The plurality of exhaust passages 114 may be disposed through inner shield 106 to allow the exhaust fluid a sufficient time to contact the sensing element 10,100 prior to exiting the protective casing 120. The plurality of exhaust passages 114 can be any size or shape sufficient to allow the passage of exhaust fluid.

Suitable materials for the protective casing 120 can include material that is capable of resisting under-car salt, temperature, and corrosion. For example, ferrous materials are employed such as ferritic stainless steels. Ferritic stainless steels may include stainless steels such as, e.g., SS-409, SS-316, and the like.

A catalyst 15 can be disposed in the exhaust stream, upstream from the first sensing cell 12/16/14. The catalyst 15 can comprise material(s) capable of converting hydrocarbons, carbon monoxide, ammonia, and/or hydrogen into water, nitrogen, and/or carbon dioxide. In one embodiment, the catalyst 15 comprises a material that, under the operating conditions of sensing element 10,100, is capable of efficiently converting NO to $NO_2$. In a second embodiment, the catalyst 15 can comprise material(s) that, under the operating conditions of the sensing element 10, are capable of converting $NO_2$ to NO. The catalyst 15 can comprise materials including platinum, platinum alloys, and the like, as well as combinations comprising at least one of the foregoing. The catalyst 15 can further comprise zeolite(s) (e.g., alumina-silica zeolite powder).

The catalyst 15 can be disposed proximate various locations in the casing 120. In general, the catalyst 15 can be disposed at a location in which the sample gas can sufficiently contact the catalyst 15 upstream from the sensing element 10,100. For example the catalyst 15 can be disposed proximate the sampling tube 110 or can be disposed proximate the inner surface of the inner shield 106. The catalyst 15 can also be disposed outside the casing 120 upstream from the sensing element 10,100. For example, the catalyst 15 could part of a catalyst bed reactor, upstream from the inlet 112 of the casing 120. In an exemplary embodiment, the sensing element 10 is disposed in an exhaust stream in fluid communication with engine exhaust. In addition to $NH_3$, $O_2$, and NOx, the sensor's operating environment includes other combustion by-products, for example, hydrocarbons, hydrogen, carbon monoxide, water, sulfur, sulfur-containing compounds, and/or combustion radicals (such as hydrogen and hydroxyl ions), and the like.

The sensing element 10 can be formed using various ceramic processing techniques. For example, milling processes (e.g., wet and dry milling processes including ball milling, attrition milling, vibration milling, jet milling, and the like) can be used to size ceramic powders into desired particle sizes and desired particle size distributions to obtain physical, chemical, and electrochemical properties. The ceramic powders can be mixed with plastic binders to form various shapes. For example, the structural components (e.g., insulating layers 22, 24, 28, 34, 36, and 38 and the active or electrolyte layers 16, 26, 30, 32) can be formed into "green" tapes by tape-casting, role-compacting, or similar processes. The non-structural components (e.g., the first electrode 12, the second electrode 18, the reference electrodes 14, 20, the electrical leads, and the contact pads) can be formed into a tape or can be deposited onto the structural components by various ceramic processing techniques (e.g., sputtering, painting, chemical vapor deposition, screen-printing, stenciling, and the like).

In one embodiment, the first electrode material is prepared and is disposed onto the electrolyte (or the layer adjacent to the electrolyte). In this method, the primary material, preferably in the form of an oxide, is combined with the dopant secondary material and optional other dopants, if any, simultaneously or sequentially. By either method, the materials are preferably well-mixed to enable the desired incorporation of the dopant secondary material and any optional dopants into the primary material to produce the desired NOx-selective material. For example, $Tb_4O_7$ is mixed with MgO and $Cr_2O_3$ by milling for about 2 to about 24 hours. The mixture is fired to about 1,000° C. for a sufficient period of time to allow the metals to transfer into the oxide structure and produce the new formulation (e.g., $TbCr_{0.8}Mg_{0.2}O_{2.9-x}$(wherein x is the difference in the value between the stoichiometric amount of oxygen and the actual amount)), which is the reaction product of the primary material, secondary material, and optional chemical stabilizing dopant, and/or diffusion impeding dopant. In a similar manner, $TbCr_{0.8}Sr_{0.2}O_3$ (a material used in the sensor in the test for FIG. 6), can be formed.

The inlets 94, 95, 96, 98, can be formed either by disposing fugitive material (material that will dissipate during the sintering process, e.g., graphite, carbon black, starch, nylon, polystyrene, latex, other insoluble organics, as well as compositions comprising one or more of the foregoing fugitive materials) or by disposing material that will leave sufficient open porosity in the fired ceramic body to allow gas diffusion therethrough. Once the "green" sensor is formed, the sensor can be sintered at a selected firing cycle to allow controlled burn-off of the binders and other organic materials and to form the ceramic material with desired microstructural properties.

The first NOx sensing cell 12/16/14 and the second NOx sensing cell 18/16/20 can generate emf as described by the Nernst Equation. In the exemplary embodiment, the sample gas is introduced to the sensing electrode(s) and is diffused throughout the porous electrode materials. In the sensing electrode(s), catalytic materials induce catalytic reactions in the sample gas. These reactions include catalyzing $NO_2$ to form NO and $H_2O$ and catalyzing NO and $O^{-2}$ to form $NO_2$. Similarly, in the reference electrode 14, 20, catalytic material induces catalytic reactions in the reference gas, converting equilibrium oxygen gas ($O_2$) to oxide ions ($O^{-2}$) or vice versa, and thereby producing an electromotive force. Therefore, the electrical potential difference between any the sensing electrode(s) 12, 18, and the corresponding reference electrode(s) 14, 20 can be measured to determine an electromotive force.

Figure 5:
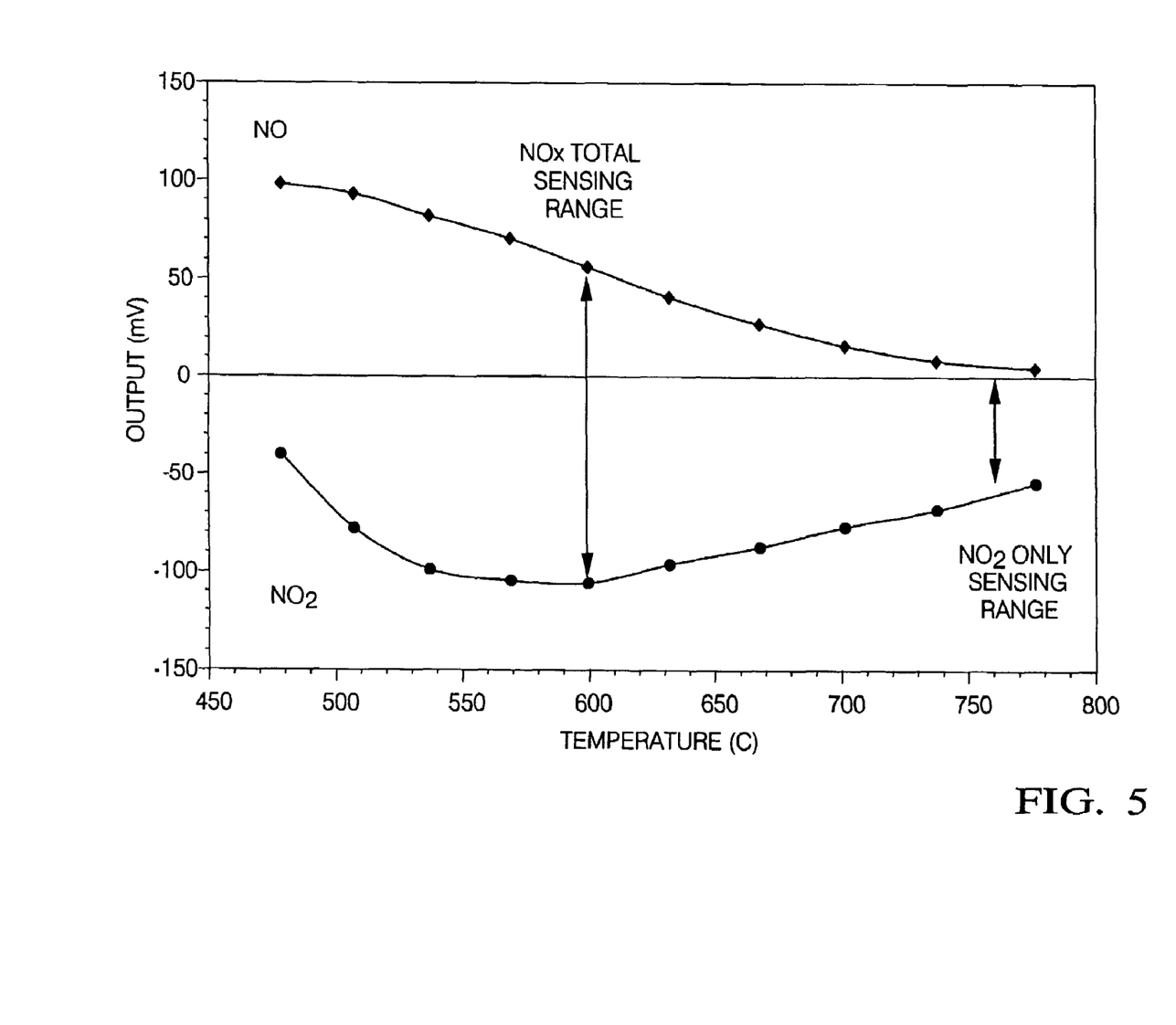
FIG. 5 is a graphical representation of sensing emf output versus temperature for NO and $NO_2$.
Figure 6:
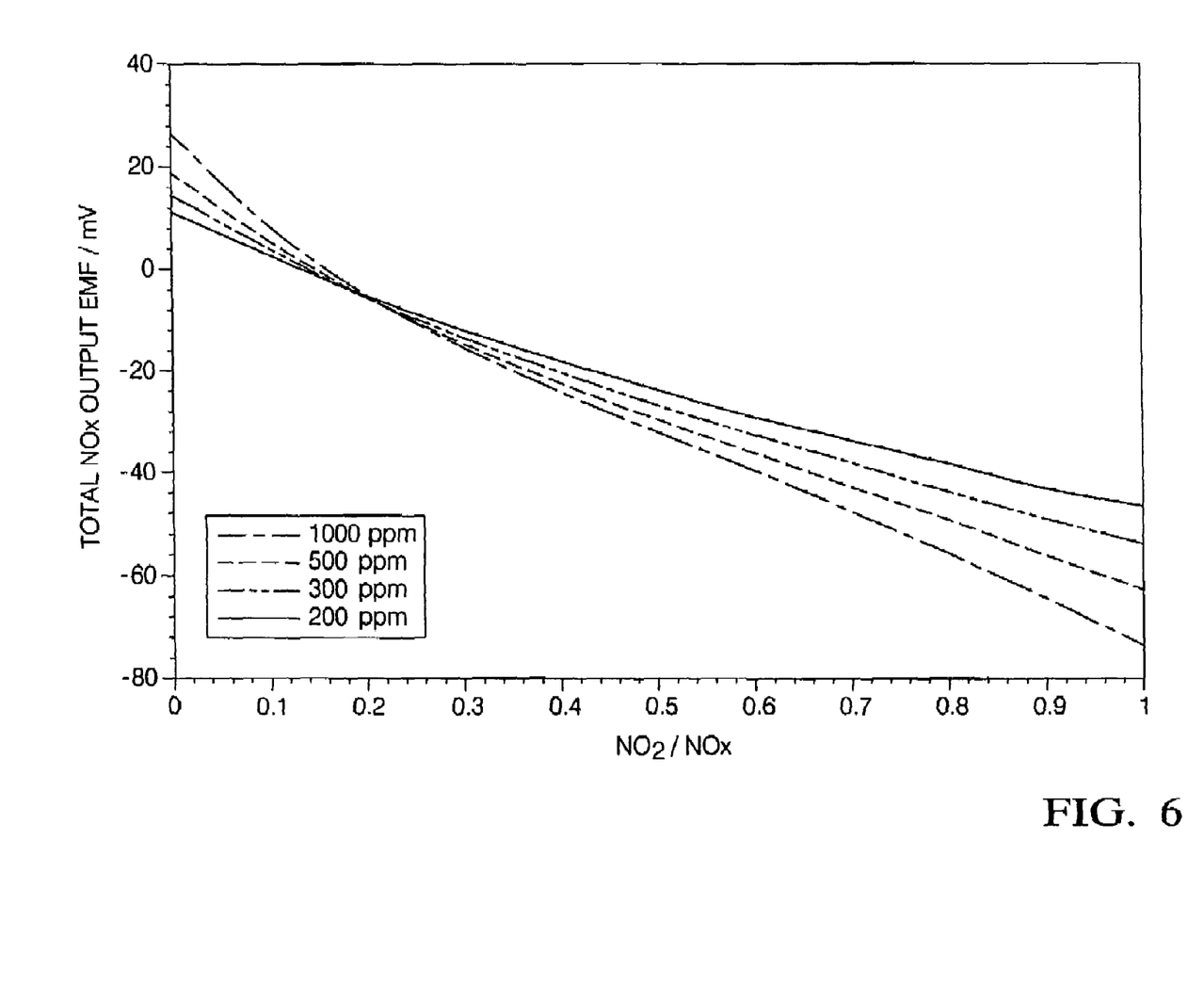
FIG. 6 is a graphical illustration of NOx performance of a sensor operated at 600° C. with the emf plotted against the ratio of $NO_2$ to NO with constant NOx at 200 ppm, 300 ppm, 500 ppm, and 1,000 ppm.

The NO sensing performance is similar except the emf is opposite to that of $NO_2$ emf; both emf are function of temperature. In FIG. 5, the sensing emf outputs for NO and $NO_2$ gas are illustrated. Both gas concentrations were set at 1,000 parts per million (ppm) by volume. It is obvious that the sensing ranges are different between NO and $NO_2$. As clearly shown in this figure, at high temperature, the sensor is a $NO_2$ selective sensor and is not sensitive to NO. At lower temperature, the sensor responds to both NO and $NO_2$. As is shown in FIG. 6; however, the sensor output depends on the composition of the NOx.

Figure 7:
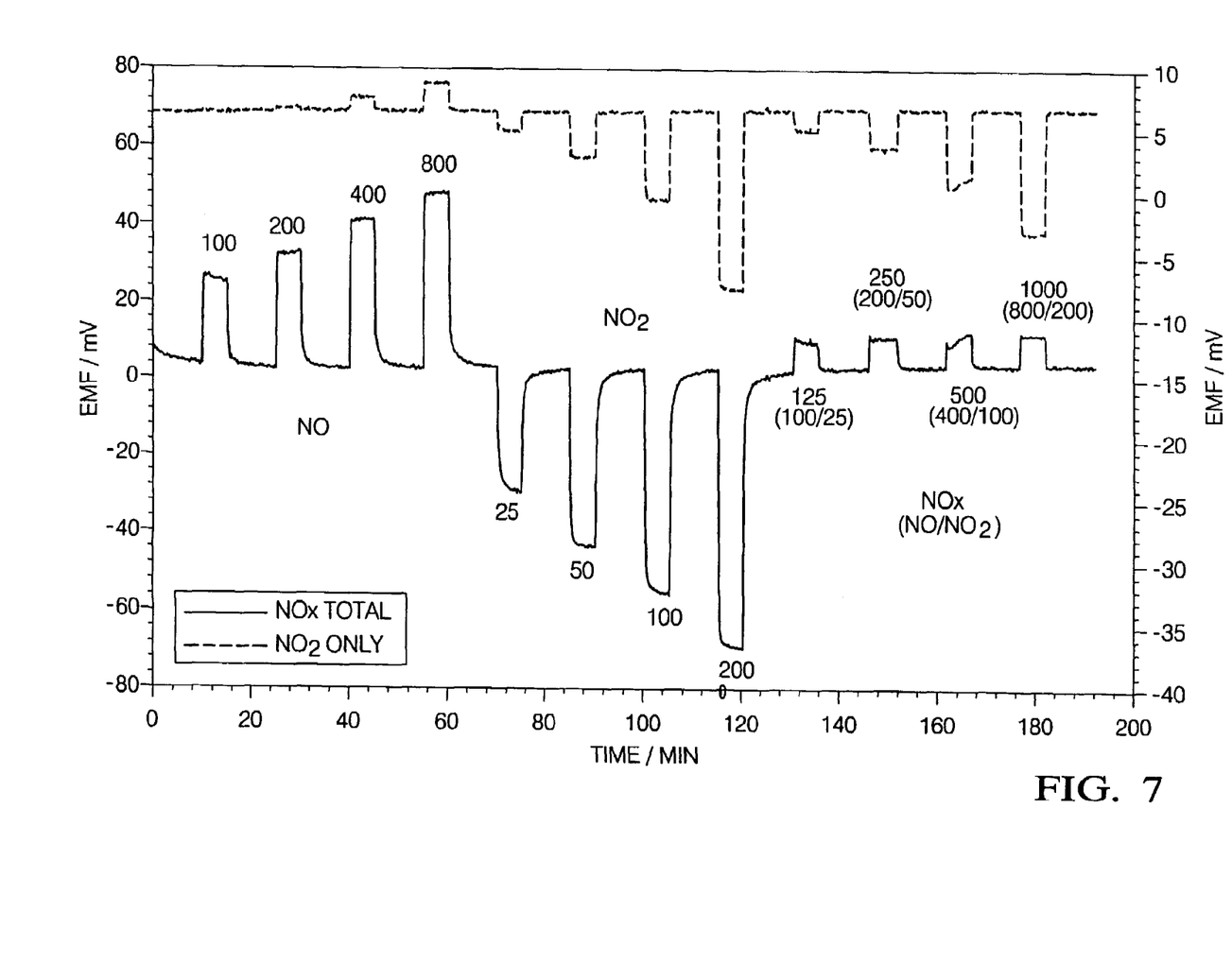
FIG. 7 is a graphical illustration of NOx sensor performance of a sensor operated at 600° C. The emf output (bottom curve) is plotted against time with the corresponding delivery of NOx presented in the same figure (top curve).

For a given NOx mixture gas, the composition of the NOx can be sensed by operating one sensor at high temperature (where, essentially, only the $NO_2$ is measured) and the other sensor at lower temperature where the NOx is measured. With the two emf outputs and the assistance of a lookup table, it is possible to determine the NO and $NO_2$ concentration of the gas mixtures. In FIG. 7, emf data for two sensors are presented where one sensor operated at high temperature (top curve) and the other at a lower temperature (bottom curve). First, NO was introduced (100 ppm; 200 ppm; 400 ppm; 800 ppm), then $NO_2$ gas was introduced (25 ppm; 50 ppm; 100 ppm; 200 ppm), and finally NOx was introduced comprising $NO/NO_2$ of 100/25 ppm, 200/50 ppm, 400/100 ppm, and 800/200 ppm.

The primary reactants at electrodes of the NOx sensing cells 12/16/14, 18/16/20 are NO, $H_2O$, $NO_2$, and $O_2$. The partial pressure of reactive components at the electrodes of the NOx sensing cell(s) can be determined from the cell's electromotive force (emf) by using the non-equilibrium Nernst Equation(1):

$$EMF \approx \frac{kT}{2e}\text{Ln}(P_{NO}) - \frac{kT}{4e}\text{Ln}(P_{O_2}) - \frac{kT}{2e}\text{Ln}(P_{H_2O}) - \frac{kT}{2e}\text{Ln}(P_{NO_2}) + \text{constant} \quad (1)$$

where: k=the Boltzmann constant
T=the absolute temperature of the gas
e=the electron charge unit
a, b, c, d are constants
Ln=natural log
$P_{NH_3}$=the partial pressure of ammonia in the gas,
$P_{O_2}$=the partial pressure of oxygen in the gas,
$P_{NO_2}$=the partial pressure of nitrogen dioxide in the gas, $P_{H_2O}$=the partial pressure of water vapor in the gas
$P_{NO}$=the partial pressure of nitrogen monoxide in the gas.

The temperature sensor can measure a temperature indicative of the absolute gas temperature (T). The oxygen and water vapor content, e.g., partial pressures, in the unknown gas can be determined from the air-fuel ratio as measured by the air-fuel sensing cell 80/26/82.

In a first embodiment, the sample gas contacts the catalyst 15. The catalyst 15 catalyzes NO to $NO_2$ so that NOx in the sample gas exists in the form $NO_2$. The heater heats the NOx sensing cell 12/16/14 to a selected operating temperature (e.g., 650° C. to 750° C.), where the electrode 12 will sense $NO_2$. The NOx sensing cell 12/16/14 generates an electromotive force based on the $NO_2$ concentration, which is indicative of the total NOx concentration of the sample gas prior to the sample gas contacting the catalyst 15. When the NO concentration is relatively low in comparison to the $NO_2$ concentration, the term $kT/2e\ Ln(P_{NO})$ can be eliminated from the equation, and the partial pressure of NO becomes the only unknown in Equation 1. Therefore, the processor can apply Equation (1) (or a suitable approximation thereof) to determine the amount of NO, or the processor can access a lookup table from which the NO partial pressure can be selected in accordance with the electromotive force output from the NOx sensing cell 12/16/14 and from the air fuel sensing cell 80/26/82.

In a second embodiment, the sample gas can optionally contact the catalyst 15. The catalyst 15 catalyzes $NO_2$ to NO so that NOx in the sample gas exists in the form NO. The heater heats the NOx sensing cell 12/16/14 to a selected operating temperature (e.g., about 200° C. to about 400° C.), where the electrode 12 will sense NO. The NOx sensing cell 12/16/14 generates an electromotive force based on the NO concentration, which is indicative of the total NOx concentration of the sample prior to the sample gas contacting the catalyst 15. When the $NO_2$ concentration is relatively low when compared with the $NO_2$ concentration, the term $kT/2e\ Ln(P_{NO})$ can be eliminated from the Equation, and the partial pressure of NO becomes the only unknown in Equation (1). Therefore, the processor can apply Equation (1) (or a suitable approximation thereof) to determine the amount of NO, or the processor can access a lookup table from which the NO partial pressure can be selected in accordance with the electromotive force output from the NOx sensing cell 12/16/14 and from the air fuel sensing cell 80/26/82.

In a third embodiment, the heater heats the sensor producing a thermal gradient across the sensing element 10. By disposing the heater adjacent the first sensing cell 12/16/14, the heater can heat the first sensing cell 12/16/14 to a first selected operating temperature (e.g., about 700° C. to about 800° C.) wherein the electrode 12 will sense $NO_2$, but not NO. The second sensing cell can operate at a second selected operating temperature (e.g., 500° C. to about 650° C.). The second sensing cell reacts with both $NO_2$ and NO, producing an emf. By using the emf from the first sensing cell and the second sensing cell, the processor can access a lookup table from which the NO partial pressure can be selected in accordance with the electromotive force output from the NOx sensing cell 12/16/14 and from the air fuel sensing cell 18/16/20. The NO partial pressure can also be determined by Equation (1) or equivalence thereof. In this embodiment, the processor can determine both the concentration of NO and the concentration of $NO_2$ in the sample gas.

The air to fuel ratio can be obtained by ECM (engine control modulus, e.g., see GB2347219A), or by having an air to fuel ratio sensor built in the sensor 10. Alternatively, a complete mapping of $H_2O$ and $O_2$ concentrations under all engine running conditions (measured by instrument such as mass spectrometer) can be obtained empirically and stored in ECM (engine control module) in a virtual look-up table with which the sensor circuitry communicates. Once the oxygen and water vapor content information is known, the processor can use the information to more accurately determine the partial pressures of the sample gas components. Typically, the water and oxygen correction according to Equation (1) is a small number within the water and oxygen ranges of diesel engine exhaust. This is especially true when the water is in the range of 1.5 weight percent (wt %) to 10 wt % in the engine exhaust. This is because the water and oxygen have opposite sense of increasing or decreasing at any given air to fuel ratio and both effects cancel each other in Equation (1). Where there is no great demand for sensing accuracy (such as±0.1 part per million by volume (ppm)), the water and oxygen correction in Equation 1 is unnecessary.

The sensor and methods described herein enable the determination of NOx concentration and, in some cases, composition. The sensor and methods can be used for OBD or control applications for diesel exhaust de-NOx after treatment systems. The sensor and methods are easy to use, cost effective to manufacture than present commercial devices.

It should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. As used herein, "combination" is inclusive of blends, mixtures, alloys, reaction products, and the like, as appropriate. The modifier "about" used in connection with a quantity is inclusive of the stated value and has the meaning dictated by the context (e.g., includes the degree of error associated with measurement of the particular quantity). Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). Finally, unless defined otherwise, technical and scientific terms used herein have the same meaning as is commonly understood by one of skill in the art to which this invention belongs. The suffix "(s)" as used herein is intended to include both the singular and the plural of the term that it modifies, thereby including one or more of that term (e.g., the metal(s) includes one or more metals). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for detecting NOx in a gas, comprising:
   contacting a first NOx electrode with the gas, wherein the first NOx electrode is at a first temperature of greater than or equal to about 700° C.;
   contacting a second NOx electrode with the gas, wherein the second NOx electrode is at a second temperature of about 500° C. to about 650° C.;
   determining a $NO_2$ emf between the first NOx electrode and a first reference electrode;
   determining a NOx emf between the second NOx electrode and a second reference electrode; and
   determining a $NO_2$ concentration and a NO concentration using the $NO_2$ emf and the NOx emf.

2. The method of claim 1, further comprising determining the A/F ratio of the gas and adjusting the NOx emf and the $NO_2$ emf based upon the A/F ratio.

3. The method of claim 1, further comprising, prior to contacting the NOx electrode with the gas, reducing a concentration of hydrocarbons, carbon monoxide, and/or hydrogen in the gas.

4. The method of claim 1, further comprising, prior to contacting the NOx electrode with the gas, forming carbon dioxide and/or water from hydrocarbons, carbon monoxide, and/or hydrogen in the gas.

5. A method for detecting NOx in a gas, comprising:
   contacting a first NOx electrode with the gas, wherein the first NOx electrode is at a first temperature of greater than or equal to about 700° C.;
   contacting a second NOx electrode with the gas, wherein the second NOx electrode is at a second temperature of about 500° C. to about 650° C.;
   determining a $NO_2$ emf between the first NOX electrode and a reference electrode;
   determining a NOx emf between the second NOx electrode and the reference electrode; and
   determining a $NO_2$ concentration and a NO concentration using the $NO_2$ emf and the NOx emf.

6. The method of claim 5, further comprising, prior to contacting the NOx electrode with the gas, reducing a concentration of hydrocarbons, carbon monoxide, and/or hydrogen in the gas.

7. The method of claim 5, further comprising, prior to contacting the NOx electrode with the gas, forming carbon dioxide and/or water from hydrocarbons, carbon monoxide, and/or hydrogen in the gas.

8. A NOx sensor element, comprising:
   a first NOx electrode, wherein the first NOx electrode is capable of operating at a first temperature of greater than or equal to about 700° C.;
   a second NOx electrode, wherein the second NOx electrode is capable of operating a second temperature of about 500° C. to about 650° C.;
   a first reference electrode;
   a second reference electrode; and
   an electrolyte, wherein the electrolyte is disposed between the first NOx electrode and the first reference electrode;
   wherein, during use, a first NOx emf can be established between the first NOx electrode and the first reference electrode, and a second NOx emf can be established between the second NOx electrode and the second reference electrode; and further wherein the first NOx electrode and/or the second NOx electrode comprises $TbCrO_3$ doped with an element selected from the group consisting of Mg, Ca, Sr, V, Ta, W, Nd, Ni, and combinations comprising at least one of the foregoing elements.

9. A NOx sensor element, comprising:
   a first NOx electrode, wherein the first NOx electrode is capable of operating at a first temperature of greater than or equal to about 700° C.;
   a second NOx electrode, wherein the second NOx electrode is capable of operating a second temperature of about 500° C. to about 650° C.;
   a first reference electrode;
   a second reference electrode; and
   an electrolyte, wherein the electrolyte is disposed between the first NOx electrode and the first reference electrode;
   wherein, during use, a first NOx emf can be established between the first NOx electrode and the first reference electrode, and a second NOx emf can be established between the second NOx electrode and the second reference electrode; and further wherein the first NOx electrode and/or the second NOx electrode comprises $TbCrO_3$ doped with an element selected from the group consisting of Co, Rh, Gd, Sn, Pb, and combinations comprising at least one of the foregoing elements.

10. A NOx sensor element, comprising:
    a first NOx electrode, wherein the first NOx electrode is capable of operating at a first temperature of greater than or equal to about 700° C.;
    a second NOx electrode, wherein the second NOx electrode is capable of operating a second temperature of about 500° C. to about 650° C.;
    a first reference electrode;
    a second reference electrode; and
    an electrolyte, wherein the electrolyte is disposed between the first NOx electrode and the first reference electrode;
    wherein, during use, a first NOx emf can be established between the first NOx electrode and the first reference electrode, and a second NOx emf can be established between the second NOx electrode and the second reference electrode; and further wherein the first NOx electrode and/or the second NOx electrode comprises $TbCrO_3$ doped with an element selected from the group consisting of Na, Ba, La, Ti, Zr, Ag, Cd, Sm, Eu, Tb, Ho, and Yb, and combinations comprising at least one of the foregoing elements.

11. A NOx sensor element, comprising:
    a first NOx electrode, wherein the first NOx electrode is capable of operating at a first temperature of greater than or equal to about 700° C.;
    a second NOx electrode, wherein the second NOx electrode is capable of operating a second temperature of about 500° C. to about 650° C.;
    a first reference electrode;
    a second reference electrode; and
    an electrolyte, wherein the electrolyte is disposed between the first NOx electrode and the first reference electrode;
    wherein, during use, a first NOx emf can be established between the first NOx electrode and the first reference electrode, and a second NOx emf can be established between the second NOx electrode and the second reference electrode; and further wherein the first NOx electrode and/or the second NOx electrode comprises $TbCrO_3$ doped with an element selected from the group consisting of K, Nb, Mn, Zn, and Er, and combinations comprising at least one of the foregoing elements.

* * * * *